United States Patent
Springston et al.

(10) Patent No.: US 7,285,243 B2
(45) Date of Patent: Oct. 23, 2007

(54) QUANTITATIVE DETERMINATION OF ATMOSPHERIC HYDROPEROXYL RADICAL

(75) Inventors: Stephen R. Springston, Upton, NY (US); Judith Lloyd, Westbury, NY (US); Jun Zheng, Stony Brook, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 319 days.

(21) Appl. No.: 10/930,587

(22) Filed: Aug. 30, 2004

(65) Prior Publication Data

US 2006/0046302 A1    Mar. 2, 2006

(51) Int. Cl.
*G01N 21/76* (2006.01)
*G01N 15/06* (2006.01)

(52) U.S. Cl. .................. 422/52; 422/68.1; 422/86; 73/31.01

(58) Field of Classification Search .............. 422/52, 422/88, 91
See application file for complete search history.

(56) References Cited

U.S. PATENT DOCUMENTS

| | | | |
|---|---|---|---|
| 3,797,999 A * | 3/1974 | Witz et al. ............ | 435/39 |
| 5,205,988 A * | 4/1993 | Tanaka et al. ........ | 422/91 |
| 6,187,277 B1 | 2/2001 | Kirschner | |
| 6,290,923 B1 | 9/2001 | Sollers et al. | |
| 6,635,415 B1 * | 10/2003 | Bollinger et al. ..... | 435/4 |

OTHER PUBLICATIONS

J.H. Lee, I. N. Tang, J.B. Weinstein-Lloyd, E.B. Haiper; Improved Nonenzymatic Method for the Determination of Gas-Phase Peroxides, 1994, Environmental Science Technology, American Chemical Society, vol. 28, pp. 1180-1185.*

Judith Weinstein-Lloyd, Stephen E. Schwartz; Low-Intensity Radiolysis Study of Free-Radical Reactions in Cloudwater: H2O2 Production and Destruction, 1991, Environmental Science Technology, American Chemnical Society, vol. 25, pp. 791-800.*

Mihelcic, D. et al., "Simultaneous Measurements of Peroxy and Nitrate Radicals at Schauinsland", *J. Atmos. Chem* 16:313-335 (1993).

Creasey, D. J., et al., "Implementation and Initial Deployment of a Field Instrument for Measurement of OH and $HO_2$ in the Troposphere by Laser-Induced Fluorescence", *J. Chem. Soc., Faraday Trans.*, 93(16):2907-2913 (1997).

Shimomura, O., et al., "Evaluation of Five Imidazopyrazinone-Type Chemiluminescent Superoxide Probes and Their Application to the Measurement of Superoxide Anion Generated by *Listeria Monocytogenes*", *Anal. Biochem*, 258:230-235 (1998).

Lazrus, A. L., et al., "Automated Fluorometric Method for Hydrogen Peroxide in Air", *Anal. Chem.*, 58:594-597 (1986).

Bielski, B. H. J., et al., "Reactivity of $HO_2/O_2$ Radicals in Aqueous Solution", *J. Phys. Chem. Ref. Data*, 14:1041-1100 (1985).

Brune, W. H., et al., "Airborne in-situ OH and $HO_2$ observations in the cloud-free troposphere and lower stratosphere during SUCCESS", *Geophys. Res. Lett.*, 25:1701-1704 (1998).

(Continued)

*Primary Examiner*—Jill Warden
*Assistant Examiner*—Neil Turk
(74) *Attorney, Agent, or Firm*—Lori-Anne Neiger

(57) ABSTRACT

A method for the quantitative determination of atmospheric hydroperoxyl radical comprising: (a) contacting a liquid phase atmospheric sample with a chemiluminescent compound which luminesces on contact with hydroperoxyl radical; (b) determining luminescence intensity from the liquid phase atmospheric sample; and (c) comparing said luminescence intensity from the liquid phase atmospheric sample to a standard luminescence intensity for hydroperoxyl radical. An apparatus for automating the method is also included.

36 Claims, 2 Drawing Sheets

OTHER PUBLICATIONS

Cantrell, C. A., et al., "Dual-Inlet Chemical Amplifier for Atmospheric Peroxy Radical Measurements", *Anal. Chem.*, 68:4194-4199 (1996).

Staehelin, J., et al., "Decomposition of Ozone in Water: Rate of Initiation by Hydroxide Ions and Hydrogen Peroxide", *Environ. Sci. Technol.*, 16:676-681 (1982).

Mihelcic, D., et. al., "Numerical Analysis of ESR Spectra from Atmospheric Samples", *J. Atmos. Chem.*, 11:271-297 (1990).

Nakano, M., et al., "Chemiluminescence Probe with *Cypridina* Luciferin Analog, 2-Methyl-6-phenyl-3,7-dihydroimidazo[1,2-α]pyrazin-3-one, for Estimating the Ability of Human Granulocytes to Generate $O^-_2$" *Anal. Biochem.*, 159:363-369 (1986).

Nishida, A., et al., "A Sensitive and Specific Chemiluminescence Method for Estimating the Ability of Human Granulocytes and Monocytes to Generate $O^-_2$", *Clin. Chem. Acta*, 179:177-181 (1989).

Tanner, D. J., et al., "Selected Ion Chemical Ionization Mass Spectrometric Measurement of OH", *J. Geophys. Rel.*, 102:6415-6425 (1997).

Zheng, J., et al., "Quantitative Analysis of Hydroperoxyl Radical Using Flow Injection Analysis with Chemiluminescence Detection", *Anal. Chem.*, 75:4696-4700 (2003).

Malbon, L. G., et al., "Quantitification of Superoxide in Natural Water Systems Using Flow Injection Analysis with Chemiluminescence Detection", 223rd American Chemical Society, National Meeting (No. 120) Apr. 7-11, 2002, Orlando, Florida.

Mann, S. E., et al., "Enhanced Reactivity of Luminol in Acidic Media: Applications to the Analysis of Hydrogen Peroxide and Superoxide in Natural Waters" 211th American Chemical Society National Meeting (No. 514) Mar. 24-28, 1996, New Orleans, LA.

Boland, N. E., et al., "Flow Injection Analysis of Superoxide in Aqueous Solution: A Quantitative Determination Using the Chemiluminescent Probe MCLA", Abstracts of Papers—221st American Society National Meeting, San Diego, CA, Apr. 1-5, 2001, CHED-749.

Bielski, B. H. J., et al., "Preparation and Stabilization of Aqueous/Ethanolic Superoxide Solutions", *Anal. Biochem.*, 133:170-178 (1983).

Yumino, K., et al., "Paraquat- and Diquat-Induced Oxygen Radical Generation and Lipid Peroxidation in Rat Brain Microsomes", *J. Biochem.*, 131(4): 565-570 (2002).

Schwarz, H. A., "Free Radicals Generated by Radiolysis of Aqueous Solutions", *Chem. Educ.*, 58: 101-105 (1981).

Koga, S., et al., "Mechanism for the Generation of Superoxide Anion and Singlet Oxygen during Heme Compound-Catalyzed Linoleic Acid Hydroperoxide Decomposition", *Archives of Biochemistry and Biophysics* 289:223-229 (1991).

Weinstein-Lloyd, J. B., et al., "Hydroperoxyl Radical Detection by MCLA Chemiluminescence", 84th American Meterological Society Annual Meeting, Seattle, WA, Jan. 11-15, 2004.

Zheng, J., et al., "Development of a Chemiluminescence Method for Gas-Phase $HO_2$ Detection", *Eos. Trans. AGU 84*(46), Fall Meet. Suppl., Abstract A22G-05, 2003.

* cited by examiner

to the quantification of hydroperoxyl radical found in the atmosphere.

QUANTITATIVE DETERMINATION OF ATMOSPHERIC HYDROPEROXYL RADICAL

The present invention was made with government support under Grant No. DE-AC02-98CH10886 awarded by the U.S. Department of Energy. The United States government has certain rights in the invention.

BACKGROUND OF THE INVENTION

The present invention relates to a method of quantifying atmospheric hydroperoxyl radical. More specifically, the present invention relates to using solution phase chemiluminescence detection for the quantification of hydroperoxyl radical found in the atmosphere.

Hydroperoxyl radical in the atmosphere plays an important role in the formation and transformation of numerous atmospheric chemicals. In particular, hydroperoxyl radical plays a role in the formation of ozone, well known as a protective agent against the harmful effects of solar radiation.

Accordingly, there has been much interest in quantifying hydroperoxyl radical in the atmosphere. For example, Cantrell et al. uses a chain-amplified gas-phase process to quantify atmospheric levels of hydroperoxyl radicals. Cantrell uses the reaction of hydroperoxyl radical with NO to produce $NO_2$, the species that is ultimately measured in the method. The accuracy of the Cantrell method is dependent on precise calculations regarding the $NO_2$ amplification process. The Cantrell method is also subject to interference from such atmospheric species as ozone, peroxyacetyl nitrate (PAN), and $NO_2$.

Similarly, Creasey et al and Brune et al have shown that hydroperoxyl radical can be measured in the gas-phase by reaction of the radical with excess NO, followed by detection of hydroxyl radical using laser-induced fluorescence (LIF) at 308 nm.

Milhelcic et al report measurement of hydroperoxyl radical using ESR spectroscopy after trapping the radicals in a solid $D_2O$ matrix at 77 K. The method used by Milhelcic et al requires the use of a numerical fitting procedure that permits the quantification of $HO_2$ in the presence of organoperoxyl radical.

In addition, the detection of hydroperoxyl radical and its conjugate base, superoxide anion, in solution by reaction of the radical with certain chemiluminescent compounds, is well known. The chemiluminescence produced in solution creates a strong and readily detectable signal without the need for complex amplification procedures. Still further, chemiluminescence methods of detection of hydroperoxyl radical in solution are typically convenient and inexpensive.

The two most popular compounds used for eliciting a chemiluminescent response with hydroperoxyl radical or superoxide anion, i.e., chemiluminescent compounds, are 2-methyl-6-phenyl-3,7-dihydroimidazo[1,2-a]pyrazin-3-one (CLA) and 2-methyl-6-(p-methoxyphenyl)-3,7-dihydroimidazo[1,2-a]pyrazin-3-one (MCLA). A review of chemiluminescent compounds for the detection of hydroperoxyl radical/superoxide anion has been given by Shimomura, et al.

For example, Malbon, et al and Boland, et al report the use of MCLA for the detection of superoxide in natural water systems. The Malbon and Boland procedures quantify superoxide by use of superoxide standards. The superoxide standards are prepared by the photolysis of a benzophenone derivative in aqueous 2-propanol solution.

However, there remains a need for a method capable of quantifying atmospheric hydroperoxyl radical that is convenient, accurate, and inexpensive. For example, none of the above references apply the many benefits of solution-phase chemiluminescence methods of detection to the quantification of atmospheric hydroperoxyl radical.

Accordingly, there is a need for improved methods of quantifying atmospheric hydroperoxyl radical. In particular, there is a need for applying the many advantages of solution phase chemiluminescence detection of hydroperoxyl radical to the quantification of hydroperoxyl radical found in the atmosphere.

SUMMARY OF THE INVENTION

In one aspect, the invention relates to a method for the quantitative determination of atmospheric hydroperoxyl radical comprising: (a) contacting a liquid phase atmospheric sample with a chemiluminescent compound which luminesces on contact with hydroperoxyl radical; (b) determining luminescence intensity from the liquid phase atmospheric sample; and (c) comparing said luminescence intensity from the liquid phase atmospheric sample to a standard luminescence intensity for hydroperoxyl radical.

In one embodiment, the standard luminescence intensity for hydroperoxyl radical is known by measuring the luminescence intensity of a quantitative standard of hydroperoxyl radical. A quantitative standard is produced by exposing a substrate to irradiation from an irradiation source, wherein the irradiation source produces a known amount of hydroperoxyl radical. Preferably, the irradiation results from a nuclear decay process such as by gamma irradiation. In a preferred embodiment, the gamma irradiation results from the nuclear decay of a cobalt-60 irradiating component.

The substrate for the quantitative standard is preferably a solution containing a formate salt and water. The formate salt is preferably sodium formate. Preferably, the substrate further includes a metal ion binding agent, such as ethylenediaminetetraacetic acid (EDTA).

In a preferred embodiment, an initial quantitative standard of hydroperoxyl radical is diluted to form another quantitative standard preferably resulting in a quantitative standard of hydroperoxyl radical having a concentration of about three nanomolar hydroperoxyl radical concentration. The diluted quantitative standard is preferably stored at a temperature of approximately 0° C. In another embodiment, the dilution is in the form of a serial dilution.

Preferably, the quantitative standard is diluted into a stabilizing solution. For example, in one embodiment, the stabilizing solution is aqueous and alkaline. Preferably, the stabilizing solution has a pH of about 11. In a further embodiment, the stabilizing solution contains non-irradiated formate.

In one embodiment, the liquid phase atmospheric sample is produced by treating an atmospheric sample with a liquid phase scrubbant. The liquid phase scrubbant must be capable of dissolving atmospheric hydroperoxyl radical into said liquid phase scrubbant. In a preferred embodiment, the liquid phase scrubbant is aqueous-based. More preferably, the liquid phase scrubbant is alkaline. Even more preferably, the aqueous-based liquid phase scrubbant has a minimum pH of about 9 and a maximum pH of about 11. Still more preferably, the liquid phase scrubbant has a pH of about 9 and contains a borax buffer, wherein the borax buffer is preferably in a concentration of about 1.25 mM.

In a further embodiment, the atmospheric sample is treated with a liquid phase scrubbant in combination with a scrubbing element. The scrubbing element may be, for example, a coil, and more preferably, a glass coil.

The chemiluminescent compound is preferably 2-methyl-6-phenyl-3,7-dihydroimidazo[1,2-a]pyrazin-3-one or 2-methyl-6-(p-methoxyphenyl)-3,7-dihydroimidazo[1,2-a]pyrazin-3-one.

In a preferred embodiment, the chemiluminescent compound is a component in a chemiluminescent reagent. The chemiluminescent reagent may comprise, for example, the chemiluminescent compound and a solvent capable of dissolving the chemiluminescent compound. Such a solvent is preferably an aqueous-based solvent. In a preferred embodiment, the aqueous-based solvent is a 1:100 volume by volume solvent mixture of ethanol to water. In a further preferred embodiment, the chemiluminescent reagent has a minimum pH of about 1 and a maximum pH of about 5. More preferably, the chemiluminescent reagent has a minimum pH of about 2 and a maximum pH of about 3. Even more preferably, the chemiluminescent reagent has a pH of about 2.3. The chemiluminescent compound is preferably in a minimum concentration of about 1 micromolar and a maximum concentration of about 30 micromolar in the chemiluminescent reagent. More preferably, the chemiluminescent compound is in a concentration of about 9 micromolar in the chemiluminescent reagent.

In a preferred embodiment, the pH of each of the liquid phase atmospheric sample and the chemiluminescent compound are appropriately adjusted such that the pH of the combination is about 3.

Luminescence intensity is preferably measured with a chemiluminescence detector. In one embodiment, the luminescence intensity is the luminescence intensity at a particular wavelength of light within a range of wavelengths of light wherein luminescence occurs. In another embodiment, the luminescence intensity is the sum of the luminescence intensities measured over a range of wavelengths of light wherein luminescence occurs. Preferably, the range of wavelengths of light is a range of visible wavelengths of light. More preferably, the range of visible wavelengths of light span about 380 to 700 nanometers.

In another embodiment, the method for the quantitative determination of atmospheric hydroperoxyl radical is automated by use of a flow injection apparatus. In yet another embodiment, the liquid phase atmospheric sample is produced continuously by a continuous flow of atmosphere into a scrubbing station.

In another aspect, the invention is directed to an apparatus for the quantitative determination of atmospheric hydroperoxyl radical. The apparatus includes (i) a source of a liquid phase atmospheric sample which includes a conduit for directing said liquid phase atmospheric sample; (ii) a source of a chemiluminescent compound in a reagent stream which includes a conduit for directing said reagent stream; (iii) a contact zone connected for fluid flow to each said carrier stream conduit and reagent stream conduit whereby said liquid phase atmospheric sample is contacted with said chemiluminescent compound; and (iv) a chemiluminescence detector which detects luminescence resulting from said contact.

Preferably, the apparatus further includes a carrier stream. The carrier stream preferably comprises a solvent capable of dissolving hydroperoxyl radical. Preferably, such a solvent is aqueous-based. More preferably, such a solvent is alkaline. Even more preferably, the carrier stream further comprises a formate salt, such as sodium formate, and is alkaline. Even more preferably, the carrier stream has a minimum pH of about 9 and a maximum pH of about 11.

The pH of the carrier stream is adjusted with a base such as sodium hydroxide. In another embodiment, the carrier stream is an aqueous-based and alkaline solution of borax having a pH preferably of about 9.

In a preferred embodiment, the reagent stream comprises a solvent capable of dissolving the chemiluminescent compound. Preferably, such a solvent is aqueous-based. More preferably, such a solvent is a 1:100 volume by volume ethanol to water mixture. The reagent stream preferably has a pH of about 1 to 3, more preferably, a pH of about 2.3.

Preferably, the apparatus described herein uses the preferred chemiluminescent compounds described above. Preferably, the chemiluminescent compound is in a minimum concentration of about 1 micromolar and a maximum concentration of about 30 micromolar in the chemiluminescent reagent. More preferably, the chemiluminescent compound is in an amount of about 9 micromolar.

In a preferred embodiment, the conduit for directing each of the carrier stream and the reagent stream comprises a fluid pump coupled to a fluid director. The fluid director is preferably a tube. The fluid pump may be, for example, a peristaltic pump.

Preferably, the fluid pump directs the carrier stream and reagent stream at specified flow rates. More preferably, the flow rates are adjustable. For example, the specified flow rates are preferably independently about 0.5 to 3.0 milliliters per minute, and more preferably independently about 1.0 to 1.5 milliliters per minute.

In a preferred embodiment, the source of the liquid phase atmospheric sample comprises a scrubbing station. The scrubbing station comprises a chamber containing housing for a liquid phase scrubbant. The housing is connected to both an inlet for atmosphere and an air pump having an air outlet. The housing further contains means for delivery of the liquid phase scrubbant. The inlet for delivery of the liquid phase scrubbant may be, for example, an injection valve or port. The housing is further connected to the conduit for directing the liquid phase atmospheric sample.

Preferably, the scrubbing station further includes a scrubbing element. The scrubbing element preferably comprises a coil, preferably a glass coil. In a preferred embodiment, the coil contains five to twenty rounds of coilings.

In another embodiment, the coil has means for adjusting the coil temperature. The coil temperature may be adjusted by, for example, the flow of a cooling or heating liquid or gas housed within the coil.

In a preferred embodiment, the apparatus further includes a mixing station wherein the carrier stream and reagent stream are mixed to form a liquid phase atmospheric sample-chemiluminescent compound mixture. In a further preferred embodiment, the mixing station is within the chemiluminescence detector. Preferably, the carrier stream-reagent stream mixture has a pH of about 3.

The apparatus may further include electronics for processing the luminescence intensity. For example, the apparatus may include a computer or computer system.

DETAILED DESCRIPTION

Figure 1:
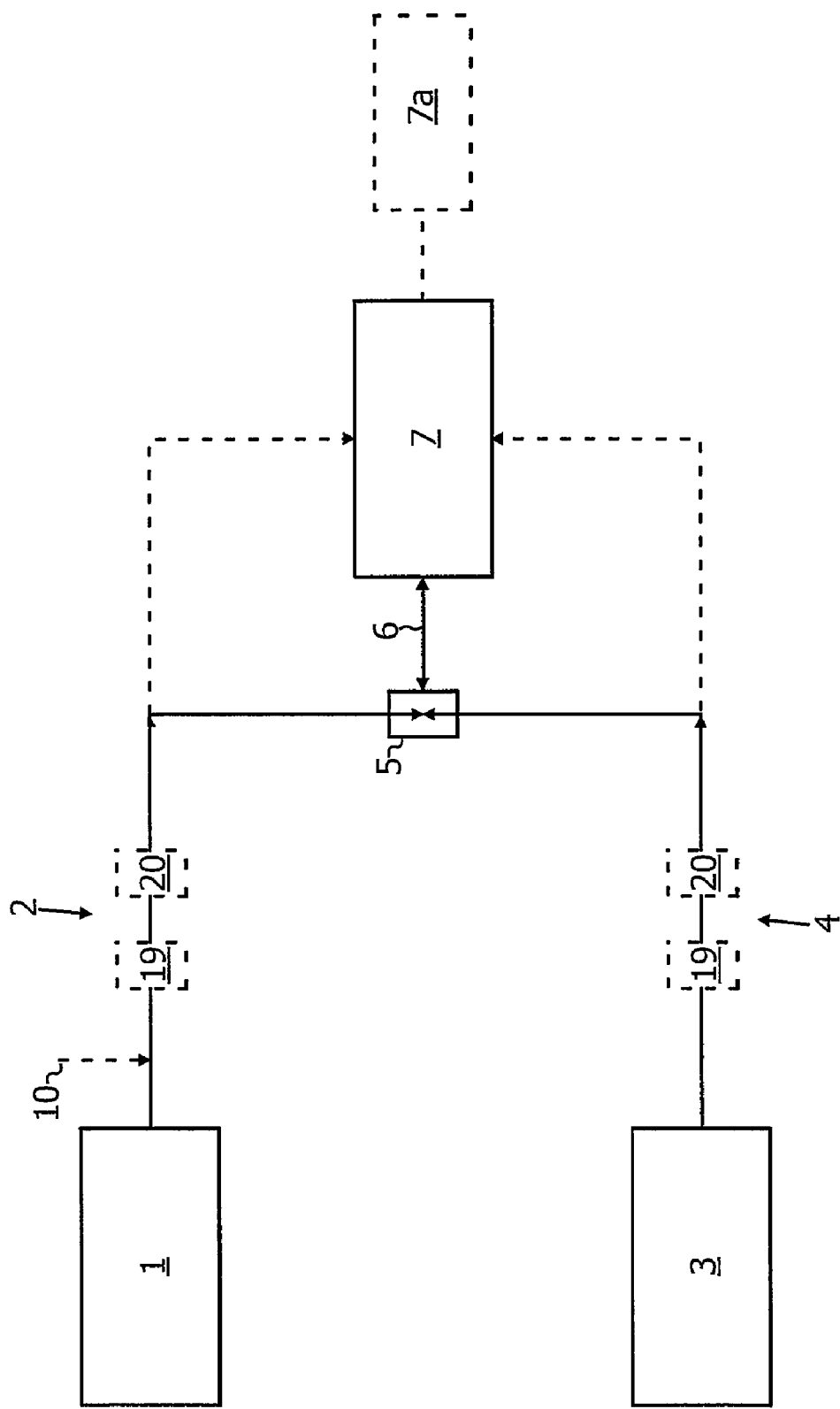
FIG. 1 is a schematic representation of a preferred apparatus for automating the method of the invention.

The present invention relates to a method for the quantitative determination of atmospheric hydroperoxyl radical. The term "atmospheric hydroperoxyl radical" refers herein particularly to hydroperoxyl radical found outdoors from ground level to the upper limits of the atmosphere. However, atmospheric hydroperoxyl radical also refers to hydroperoxyl radical in essentially any gaseous sample, such as, for example, indoor or underground gas samples.

In the method, atmospheric hydroperoxyl radical may be quantified numerically or non-numerically. When quantified numerically, the quantity of atmospheric hydroperoxyl radical is expressed in terms of a numerical value. The numerical value of quantity may be expressed as a concentration in solution, such as molarity. For example, the quantity of atmospheric hydroperoxyl radical found in solution may be expressed as 100 picomolar, i.e., 100 pM, or equivalently as $1 \times 10^{-10}$ M. From the molarity, the quantity may alternatively be expressed, for example, as a molality or weight by weight parts per million (ppm), parts per billion (ppb), parts per trillion (ppt), and so on.

Alternatively, the numerical value of quantity found in solution may be expressed as a value corresponding to the quantity of hydroperoxyl radical in the atmospheric sample. By knowing the volume of the atmospheric sample taken, and the total number of moles of hydroperoxyl radical in solution, the molar quantity of hydroperoxyl radical per volume of atmospheric sample is calculated. Quantities of hydroperoxyl radical in the gas phase may thus be expressed as parts per million by volume (ppmv), parts per billion by volume (ppbv), parts per trillion by volume (pptv), and so on.

When quantified non-numerically, the quantity of atmospheric hydroperoxyl radical may be indicated as below or above a specified limit, or below, above, or within a specified range of a quantity of hydroperoxyl radical. The non-numeric indication of a quantity of hydroperoxyl radical may be in the form of a phrase, such as "accelerated," "normal," or "acceptable", etc., as compared to a known or established limit or range. Alternatively, the non-numeric indication of a quantity of hydroperoxyl radical may be in the form of a signal, such as a light or sound, or a combination thereof.

Hydroperoxyl radical, $HO_2$, is one of many chemical species in the atmosphere. The atmosphere is composed of several layers, including the exosphere, mesosphere, stratosphere, thermosphere, and troposphere layers, all of which may contain some level of hydroperoxyl radical. The troposphere contains most of the earth's atmosphere, and is therefore, the area of the atmosphere of utmost consideration in the present invention.

In the gas-phase, equilibration of $HO_2$ with its conjugate base, superoxide anion, $O_2^-$, is expected to be minor. However, in most liquid phases, $HO_2$ equilibrates appreciably with superoxide. For example, in aqueous solutions, the equilibration is known to be extremely rapid. Thus, in view of the equilibration of hydroperoxyl radical with superoxide anion, the term "hydroperoxyl radical" as used herein, includes the superoxide anion.

According to the invention, a liquid phase atomospheric sample is produced by treating an atmospheric sample with a liquid phase scrubbant. The "liquid phase scrubbant" is a liquid phase that dissolves gaseous hydroperoxyl radical.

In a preferred embodiment, the liquid phase scrubbant is capable of dissolving most, and more preferably, essentially all, of the hydroperoxyl radical in an atmospheric sample. By "essentially all" is meant the total amount of hydroperoxyl radical in the atmospheric sample as is reasonably understood in the art. It is understood, that for gas and liquid phases in intimate contact, a certain amount of the gas-phase species under study will remain in the gas phase due to the known partitioning between phases according to Henry's Law.

In one embodiment, the liquid phase scrubbant is a solvent or solvent mixture. The solvent or solvent mixture includes, for example, alcohols, organic solvents, and inorganic solvents. Some examples of alcohols include methanol, ethanol, isopropanol, butanol, and the like, and combinations thereof. Some examples of organic solvents include toluene, xylenes, benzene, dimethylsulfoxide, hexanes, ethylene glycol, propylene glycol, dimethylformamide, chloroform, diethyl ether, methyl t-butyl ether, supercritical carbon dioxide, and the like, and combinations thereof. An example of an inorganic solvent includes sulfur dioxide.

In a preferred embodiment, the solvent or solvent mixture of the liquid phase scrubbant is aqueous-based. Some examples of aqueous-based solvents and solvent mixtures include, for example, water, alcohol-water mixtures, and water-organic solvent mixtures. Some examples of alcohol-water mixtures include 1:1 volume by volume water to ethanol, 2:1 volume by volume water to isopropanol, 3:1 volume by volume water to isopropanol, and 10:1 volume by volume water to butanol. Some examples of water-organic solvent mixtures include mixtures of chloroform and water, acetone and water, dimethylsulfoxide and water, and dimethylformamide and water.

In another embodiment, the liquid phase scrubbant is a liquid phase solution. Some examples of liquid phase solutions include sodium hydroxide and ammonium hydroxide aqueous solutions, saline aqueous solutions, borate aqueous solutions, organic amines in organic solvents or alcohols, and aqueous and alcohol solutions containing complexing agents such as ethylenediaminetetraacetic acid (EDTA) or methylsulfonic acid (MSA).

In a preferred embodiment, the liquid phase scrubbant is aqueous-based and alkaline. More preferably, the aqueous alkaline solution has a minimum pH of about 9 and a maximum pH of about 11. For example, in a preferred embodiment, the liquid phase scrubbant has a pH of about 9 and contains a borax buffer. In a further preferred embodiment, the borax buffer is in a concentration of about 1.25 mM.

In one embodiment, the liquid phase atmospheric sample is produced directly. For example, the liquid phase scrubbant also functions as the liquid phase in the sample when the sample is tested.

In another embodiment, the liquid phase atmospheric sample is produced indirectly. For example, an atmospheric sample may be treated with a first liquid phase scrubbant, followed by mixing or otherwise contacting the first liquid phase scrubbant with a second liquid phase. The first and second liquid phases may be miscible or immiscible as long as such behavior does not adversely interfere with the goals of the invention.

The purity of the solvent(s) used for the liquid phase scrubbant and any additional liquid phase(s) should be such that contaminants are at low enough levels so as not to adversely affect hydroperoxyl radical detection or quantification. For example, it is preferable that the solvent(s) do not cause a luminescence background signal.

Preferably, solvent(s) used are of a higher purity than the standard purity required for non-critical applications. For example, electronic grade purity and higher are preferable. Water is preferably purified to approximately 18.2 MOhm resistivity.

To further eliminate the possibility of an interfering background signal from the liquid phase component, a control may be run. A control can be run, for example, by running the method on a liquid phase blank, i.e., liquid phase that does not contain hydroperoxyl radical. Any background signal from the liquid phase blank can be negated in future experiments by use of a correction factor. Alternatively, a higher purity level solvent may be used that does not cause a background signal.

In a preferred embodiment, the liquid phase atmospheric sample is produced by treating an atmospheric sample with a liquid phase scrubbant in combination with a scrubbing element. Some examples of scrubbing elements known in the art include bubblers, impingers, wetted wicks, and surface spreaders.

A surface spreader increases the surface area of a liquid phase scrubbant by spreading the liquid phase scrubbant onto its surface. Such surface spreading increases contact of the liquid phase scrubbant with the atmospheric sample, and hence, increases the ability of the liquid phase scrubbant to dissolve atmospheric species such as hydroperoxyl radical. Surface spreaders may be in the form of a variety of shapes, for example, rectangular and cylindrical blocks, tubes, spheres, beads, and mesh. The surface spreaders may be solid or hollow, and may be made of any material that does not interfere with the method. Some examples of materials that may be used for surface spreading include glass, metal, ceramics, and plastic.

In a preferred embodiment, the scrubbing element is a coil. An advantage of using a coil is that the effects of modifications in a coil on the process are generally well understood.

In a preferred embodiment, the scrubbing element is a glass coil. The glass coil may be modified to contain an optimal number of rounds, for example, five to twenty rounds. In a preferred embodiment, the glass coil contains ten rounds.

Preferably, to ensure full solvating ability of a liquid phase scrubbant, at least in the initial run, the atmospheric sample is scrubbed for a specified period of time until a level state of chemiluminescence intensity is observed. Alternatively, the scrubbing time is kept constant and the scrubbing coil lengthened appropriately until a level state of chemiluminescence intensity is observed. Other modifications may be made, as necessary, to ensure full solvating ability by the liquid phase.

In another embodiment, the liquid phase scrubbant is not required to dissolve most, or all, of the atmospheric hydroperoxyl radical. The foregoing embodiment may be preferred in those situations where comparative amounts are desired to be calculated, as opposed to absolute amounts.

In order to quantify hydroperoxyl radical in the liquid phase atmospheric sample according to the present invention, the liquid phase atmospheric sample must first be contacted with a chemiluminescent compound. The liquid phase atmospheric sample can be contacted with the chemiluminescent compound in any manner that does not interfere with the goals of the invention.

For example, a solution containing the liquid phase atmospheric sample can be mixed with a solution containing the chemiluminescent compound. Mixing can be performed, for example, by hand, or more preferably, mechanically, by, for example, a flow injection apparatus. Alternatively, the liquid phase atmospheric sample can be contacted with the chemiluminescent compound by applying one onto the other on a surface, such as a section of filter paper, a slide of glass, or a well. The chemiluminescent compound may also be in the form of a solid, i.e., not in solution, when combined with the liquid phase atmospheric sample.

The chemiluminescent compounds of the present invention must be able to luminesce when contacted with hydroperoxyl radical or its conjugate base, superoxide anion. In one embodiment, the luminescence occurs by direct contact with hydroperoxyl radical or superoxide anion. In another embodiment, the luminescence occurs indirectly, for example, by contact with a reaction product of hydroperoxyl radical.

Preferably, the chemiluminescent compounds luminesce in the presence of hydroperoxyl radical in a reasonably selective manner. By "reasonably selective" is meant the observed luminescence is attributed predominantly to the presence of hydroperoxyl radical, and not to other chemical species.

Luminescence due to species other than hydroperoxyl radical or its reaction products, i.e., interfering species, is a cause of background signal. A host of interfering species exist, including hydroxyl radical and ozone.

It is known that a chemiluminescent compound used for hydroperoxyl radical detection will generally have some degree of background signal due to one or more interfering species. When desired, a correction factor may be used when the method uses chemiluminescent compounds that exhibit an interference or background signal that interferes with the method. The correction may be based on what is known in the art, or what has been determined experimentally, by, for example, running controls.

Some of the more popular chemiluminescent compounds known in the art include luminol and the imidazopyrazinone class of compounds. Some of the more preferred chemiluminescent compounds of the present invention include 2-methyl-6-phenyl-3,7-dihydroimidazo[1,2-a]pyrazin-3-one (CLA) and 2-methyl-6-(p-methoxyphenyl)-3,7-dihydroimidazo[1,2-a]pyrazin-3-one (MCLA), members of the imidazopyrazinone class of compounds.

In particular, an advantage of MCLA is its high sensitivity. Thus, low concentrations of MCLA may be used to attain an adequate or strong signal with an increased signal to background ratio.

When appropriate, the chemiluminescent compound may be used in isolated form. Alternatively, the chemiluminescent compound is a component in a chemiluminescent reagent. For example, the chemiluminescent reagent may at least include the chemiluminescent compound and a solvent or solvent mixture. The solvent or solvent mixture must be capable of dissolving the chemiluminescent compound. The solvent may be a pure solvent, a solvent mixture, or a component of a solution.

In a preferred embodiment, the solvent in the chemiluminescent reagent is an aqueous-based solvent. For example, the chemiluminescent reagent may include the chemiluminescent compound in a 1:100 volume by volume solvent mixture of ethanol to water; a 1:50 volume by volume solvent mixture of ethanol to water; a 1:100 volume by volume solvent mixture of isopropanol to water; and the like.

In a further preferred embodiment, a chemiluminescent reagent containing MCLA or CLA has a minimum pH of about 1 and a maximum pH of about 5. More preferably, the chemiluminescent reagent containing MCLA or CLA has a minimum pH of about 2 and a maximum pH of about 3. Most preferably, the chemiluminescent reagent containing MCLA or CLA has a pH of about 2.3. The pH of the chemiluminescent reagent may be adjusted by use of an acid, such as, for example, hydrochloric acid, or by a base, such as, for example, sodium hydroxide.

The chemiluminescent compound is used in a concentration that does not interfere with the goals of the experiment. For example, for MCLA or CLA, the concentration is preferably a minimum of about 1 micromolar and a maximum of about 30 micromolar in the chemiluminescent reagent. More preferably, the MCLA or CLA compound is in a concentration of about 9 micromolar in the chemiluminescent reagent. Preferably, the injection volume of the chemiluminescent reagent is about 50 to 500 microliters. More preferably, the injection volume of the chemiluminescent reagent is about 200 microliters.

In a preferred embodiment, the combination of the liquid phase atmospheric sample and the chemiluminescent compound has a minimum pH of about 2 and a maximum pH of about 4. More preferably, the combination has a pH of about 3. Accordingly, the pH of each of the liquid phase atmospheric sample and the chemiluminescent compound are appropriately adjusted.

The intensity of luminescence from each of the liquid phase atmospheric sample and the quantitative standard of hydroperoxyl radical is preferably measured with a chemiluminescence detector. The chemiluminescence detector must be capable of measuring the intensity of luminescence and must not otherwise interfere with the goals of the invention. A host of commercially available chemiluminescence detectors are suitable for the present invention.

After the chemiluminescent compound is contacted with the liquid phase atmospheric sample, a steady decrease in signal typically occurs. The decrease in signal is believed to be due to decomposition of both hydroperoxyl radical and the chemiluminescent compound. Therefore, preferably, the luminescence signal is measured as soon as possible after contacting the chemiluminescent compound with the liquid phase atmospheric sample. Accordingly, it is advantageous, but by no means required, to use a chemiluminescence detector that has a mixing feature for mixing the liquid phase atmospheric sample and chemiluminescent reagent at the time of signal measurement.

In order to quantify the amount of hydroperoxyl radical in an atmospheric sample, the luminescence intensity determined for the liquid phase atmospheric sample is compared to a standard luminescence intensity. Such a standard luminescence intensity may be known in the art, or may be determined or verified as described below.

In a preferred embodiment, a standard luminescence intensity for hydroperoxyl radical is determined by measuring the luminescence intensity of a quantitative standard of hydroperoxyl radical. The quantitative standard may be in the form of a liquid phase solution, or alternatively, a gas phase solution.

The majority of methods known for producing hydroperoxyl radical rely on the chemical transformation of a chemical species, i.e., a substrate, by exposure of the substrate to an energy source. The energy source may be, for example, ultraviolet (UV) irradiation or irradiation resulting from a nuclear decay process, such as alpha, beta, or gamma irradiation. For example, some methods known in the art for producing hydroperoxyl radical include the gamma irradiation of formate, methanol, ethanol, 2-propanol, or hydrogen peroxide. Other methods include the xanthine oxidase reaction with either xanthine or acetaldehyde, as well as UV photolysis of solutions of hydrogen peroxide.

A quantitative standard of hydroperoxyl radical must contain a known amount of hydroperoxyl radical. In a preferred embodiment, the amount of hydroperoxyl radical in a liquid phase quantitative standard is known by correlating irradiation intensity applied to the substrate to amount of hydroperoxyl radical produced. For example, it is known that when a 1.5 mM sodium formate solution is irradiated with $^{60}$Co gamma radiation of 2.77 rads per minute intensity, $HO_2$(aq) radicals are produced at a rate of approximately 0.290 μM per minute. The concentration of hydroperoxyl radical may be verified spectrophotometrically ($\epsilon_{240}$=2300 $Lmol^{-1}cm^{-1}$).

In a preferred embodiment, the substrate for irradiation is a solution comprising a formate salt and water. Examples of formate salts include lithium formate, sodium formate, potassium formate, ammonium formate, and the like. In a preferred embodiment, the formate salt concentration is a minimum of about 1.0 millimolar and a maximum of about 2.0 millimolar. More preferably, the formate salt concentration is about 1.5 millimolar.

Preferably, the substrate solution to be irradiated further includes a metal ion binding agent, such as, for example, EDTA. In a preferred embodiment, the metal binding agent is in a concentration of about 5 micromolar. For the case of formate solution, it is preferable that the pH be a minimum of about 9 and a maximum of about 11. More preferably, the formate solution has a pH of about 11. It is also preferred that the formate solution be air saturated.

In one embodiment, the irradiated substrate serves as the quantitative standard of hydroperoxyl radical. In another embodiment, the irradiated substrate serves as an initial quantitative standard, which is then diluted to produce new or additional standard(s). Preferably, the dilution results in a quantitative standard of hydroperoxyl radical having a concentration of about 1 to 10 nanomolar hydroperoxyl radical concentration. More preferably, the quantitative standard of hydroperoxyl radical has a concentration of about 3 nanomolar hydroperoxyl radical concentration. Such a dilution is preferably achieved by diluting the initial quantitative standard by a factor of about one hundred.

Alternatively, multiple dilutions, as in the form of a serial dilution, serve as quantitative standards of hydroperoxyl radical. For example, an initial quantitative standard of about 500 nanomolar hydroperoxyl radical may be diluted to produce 400, 300, 200, 100 nanomolar standards. The 100 nanomolar standard may in turn be diluted to, for example, 90, 80, 70, 60, 50, 40, 30, 20, and 10 nanomolar standards.

When diluting the initial quantitative standard of hydroperoxyl radical, a stabilizing solution is preferably used as the diluent. Preferably, the stabilizing solution is capable of stabilizing hydroperoxyl radical for a period of at least about 1 hour. More preferably, the stabilizing solution is capable of stabilizing hydroperoxyl radical for a period of at least about 8 hours. To further improve stability, the diluted standard may be stored at a temperature of approximately 0° C.

In a preferred embodiment, the solution used for stabilizing and/or storing hydroperoxyl radical of a quantitative standard is an aqueous solution of non-irradiated formate with a pH of about 11. The pH may be adjusted using an appropriate amount of a base, such as, for example, sodium hydroxide.

In one embodiment, luminescence intensity is measured at a particular wavelength of light. The particular wavelength of light is within a range of wavelengths wherein luminescence occurs. Since luminescence intensity varies according to wavelength, it is preferable that the measured intensity in both the liquid phase sample and standard be from the same wavelength of light.

In a preferred embodiment, luminescence intensity is the sum of the luminescence intensities measured over a range of wavelengths of light wherein luminescence occurs. More preferably, the range of wavelengths of light is a range of visible wavelengths of light. Even more preferably, the range of visible wavelengths of light span about 380 to 700 nanometers. Each of the liquid phase sample and standard is preferably measured in the same range of wavelengths.

In another aspect, the invention is directed to an apparatus for the quantitative determination of atmospheric hydroperoxyl radical. The apparatus includes (i) a source of a liquid phase atmospheric sample which includes a conduit for directing said liquid phase atmospheric sample; (ii) a source of a chemiluminescent compound in a reagent stream which includes a conduit for directing said reagent stream; (iii) a contact zone connected for fluid flow to each said carrier stream conduit and reagent stream conduit whereby said liquid phase atmospheric sample is contacted with said chemiluminescent compound; and (iv) a chemiluminescence detector which detects luminescence resulting from said contact.

FIG. 1 provides a general illustration of an apparatus of the present invention for the quantitative determination of atmospheric hydroperoxyl radical. A source of a liquid phase atmospheric sample 1 is connected to a conduit 2 for directing said liquid phase atmospheric sample. The apparatus optionally includes a source of a carrier stream 10 connected to the conduit 2 for directing said liquid phase atmospheric sample. A source of a chemiluminescent compound 3 in a reagent stream is connected to a conduit 4 for directing said reagent stream.

In one embodiment, a contact zone 5 is connected for fluid flow to each said conduit 2 and 4 whereby said liquid phase atmospheric sample is contacted with said chemiluminescent compound to form a liquid phase atmospheric sample-chemiluminescent compound mixture. The contact zone 5 is connected for fluid flow to a conduit 6, which directs the liquid phase atmospheric sample-cheiniluminescent compound mixture to a chemiluminescence detector 7. In another embodiment, the contact zone is located inside the chemiluminescence detector 7. The chemiluminescence detector 7 is optionally connected to further electronics for processing luminescence intensity or data acquisition 7a, such as a computer or computer system. The contact zone 5 or the contact zone within the chemiluminescence detector 7 may further include a mixing station wherein the carrier stream and reagent stream are mixed to fonn a liquid phase atmospheric sample-cheiniluminescent compound mixture.

The carrier stream carries the liquid phase atmospheric sample. The carrier stream is in accordance with the description given previously for the liquid phase of the liquid phase atmospheric sample. For example, the carrier stream may be a solvent, solvent mixture, or solution capable of dissolving hydroperoxyl radical. In a preferred embodiment, the carrier stream is aqueous-based, contains a formate salt, and is alkaline. More preferably, the carrier stream has a minimum pH of about 9 and a maximum pH of about 11. The pH of the carrier stream may be adjusted with a base, such as sodium hydroxide. More preferably, the carrier stream has a pH of about 11 and a formate concentration of about 1.5 millimolar. Alternatively, the carrier stream may be an alkaline solution containing borax and having a pH of about 9.

The reagent stream carries the chemiluminescent compound. The reagent stream is in accordance with the requirements previously given for the solvent or solvent mixture in the chemiluminescent reagent. For example, the solvent or solvent mixture in the reagent stream is capable of dissolving the chemiluminescent compound. The reagent stream may, for example, be aqueous-based.

In a preferred embodiment, the reagent stream includes a 1:100 volume by volume ethanol to water mixture. Preferably, the reagent stream has a pH of about 1 to 3, more preferably a pH of about 2.3.

In a preferred embodiment, the pH of the carrier stream and the pH of the reagent stream are adjusted such that the pH of the combination is a minimum of about 2 and a maximum of about 4. More preferably, the liquid phase atmospheric sample-chemiluminescent compound combination has a pH of about 3.

In a further preferred embodiment, the chemiluminescent compound is 2-methyl-6-phenyl-3,7-dihydroimidazo[1,2-a] pyrazin-3-one or 2-methyl-6-(p-methoxyphenyl)-3,7-dihydroimidazo[1,2-a]pyrazin-3-one. Preferably, the chemiluminescent compound is in a minimum concentration of about 1 micromolar and a maximum concentration of about 30 micromolar in the chemiluminescent reagent. More preferably, the chemiluminescent compound is in an amount of about 9 micromolar aqueous solution of the chemiluminescent compound in a concentration of about 5 to 9 micromolar chemiluminescent compound.

The conduits 2 and 4 of the apparatus are components that direct the flow of liquid while not interfering with the operation of the apparatus. For example, in one embodiment, the conduits comprise a fluid pump 19 coupled to a fluid director 20. The fluid directors may be, for example, tubes or channels directly or indirectly connected to such pumps. The fluid pumps may also be peristaltic pumps.

In a preferred embodiment, conduits 2 and 4 are fluid pumps that direct the carrier stream and reagent stream at specified flow rates. Preferably, the flow rates are adjustable. The specified flow rates are preferably independently about 0.5 to 3.0 milliliters per minute. More preferably, the specified flow rates are independently about 1.0 to 1.5 milliliters per minute.

Figure 2:
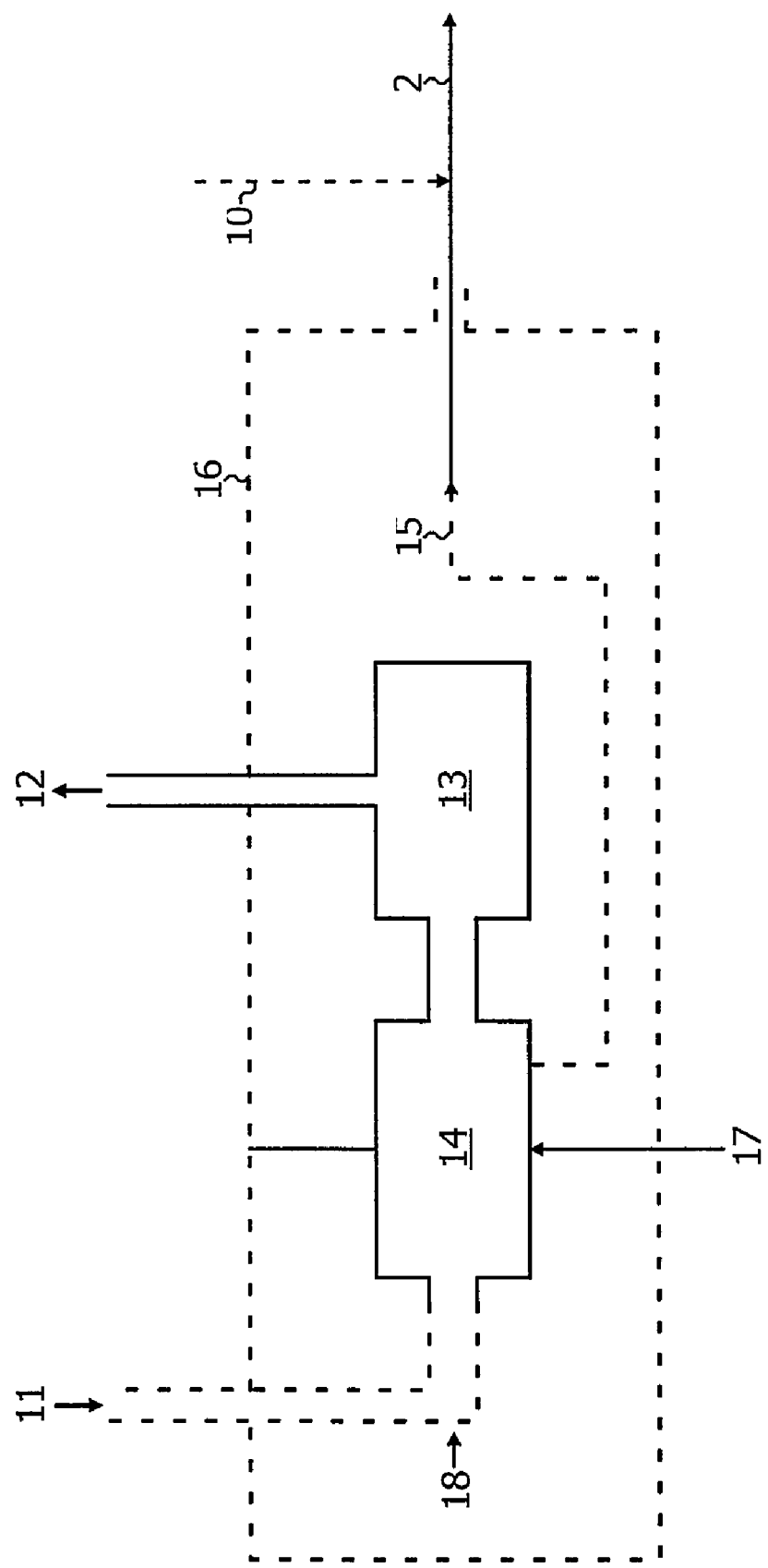
FIG. 2 is a schematic representation of a scrubbing station.

In one embodiment, the source of a liquid phase atmospheric sample 1 comprises a scrubbing station. FIG. 2 provides a general illustration of a preferred scrubbing station. The scrubbing station comprises a chamber 16 containing housing for a liquid phase scrubbant 14. The requirements for the liquid phase scrubbant is as described previously. In a preferred embodiment, the liquid phase scrubbant comprises the carrier stream.

The housing 14 is connected to both an inlet for atmosphere 11 and an air pump 13 having an air outlet 12. Optionally, housing 14 is connected to inlet 11 through an intermediary 18. The housing 14 further contains means for delivery of the liquid phase scrubbant 17 (i.e., inlet 17). Inlet 17 may be, for example, an injection valve or port. The housing 14 is connected to the conduit for directing the liquid phase atmospheric sample 2. Optionally, conduit 2 is connected to housing 14 indirectly through an optional conduit 15.

The scrubbing station 14 includes any device useful for providing a liquid phase atmospheric sample. In one embodiment, the mechanical device creates an intimate contact of a liquid phase scrubbant with an atmospheric sample. Some examples of such devices are mechanical devices, which include, but are not limited to, sprayers, misters, and vaporizers. In another embodiment, the mechanical device is a condenser. The condenser may function, for example, by producing an initial liquified atmospheric sample which is subsequently combined with a liquid phase scrubbant to make a liquid phase atmospheric sample.

In a preferred embodiment, the scrubbing station 14 includes a scrubbing element. The scrubbing element may be as described previously. In a preferred embodiment, the scrubbing element is a glass coil. The glass coil may be modified to contain an optimal number of rounds, for example, five to twenty rounds. In a preferred embodiment, the glass coil contains ten rounds.

The coil may be solid or hollow. A solid coil operates by spreading the liquid phase scrubbant on its surface. A hollow coil may operate in one of two ways. A hollow coil may operate by spreading a liquid phase scrubbant on its outer surface, in which case the atmospheric sample is external to the outer surface of the coil. Alternatively, a hollow coil may operate by spreading the liquid phase scrubbant within its inner surface, in which case the atmospheric sample is within the interior of the coil.

The scrubbing element may also have means for adjusting the temperature of the scrubbing element. For example, a glass coil may optionally have means for adjusting the coil temperature. Such temperature adjusting means include, for example, the flow of a cooling or heating liquid or gas housed within or outside a hollow coil.

The present invention is capable of quantifying atmospheric hydroperoxyl radical to at least 100 pM ($1 \times 10^{-10}$ M) when calculated according to the amount of radical in the liquid phase, or at least 0.05 pptv, when calculated according to the corresponding amount of radical in the atmospheric sample. However, the invention as described herein includes the possibility that the detection limit may be improved with the appropriate modifications.

It is well recognized that the amount of hydroperoxyl radical in a sample may be null or below the detection limit of the invention. Accordingly, the invention includes the possibility that hydroperoxyl radical is absent due to an amount of the radical that is considered null or below the measurement limit of the invention.

The invention as described herein may be appropriately modified and adjusted to conform to the unique requirements of various situations. Such modifications and adjustments are considered within the scope of the invention.

For example, it may be preferable in certain cases to practice the invention on a continuous flow of atmosphere rather than on one or more discrete atmospheric samples. A continuous flow of atmosphere may be treated with a liquid phase on a continuous basis by, for example, permitting atmosphere to continuously flow through a scrubber. As an additional example, in one embodiment, all of the method steps are performed at a single location, whereas in another embodiment, the method steps are performed in different locations, and perhaps, at different times, where applicable or desirable.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. An apparatus for the quantitative determination of atmospheric hydroperoxyl radical comprising:
  (i) a source of a liquid phase atmospheric sample which includes a carrier stream conduit for directing said liquid phase atmospheric sample within a carrier stream, wherein said liquid phase atmospheric sample is produced by treating an atmospheric sample with a liquid phase scrubbant in a scrubbing station which comprises a chamber containing housing for said liquid phase scrubbant, wherein said liquid phase scrubbant is capable of dissolving atmospheric hydroperoxyl radical, and wherein said chamber containing housing has an inlet for atmosphere, has an air outlet, and is connected to the carrier stream conduit;
  (ii) a source of a chemiluminescent compound selected from the group consisting of 2-methyl-6-phenyl-3,7-dihydroimidazo[1,2-α]pyrazin-3-one and 2-methyl-6-(p-methoxyphenyl)-3,7-dihydroimidazo[1,2-α]pyrazin-3-one in a reagent stream which includes a reagent stream conduit for directing said reagent stream wherein said reagent stream comprises an aqueous-based solvent capable of dissolving said chemiluminescent compound;
  (iii) each of said carrier stream conduit and said reagent stream conduit which are directed to a contact zone whereby said liquid phase atmospheric sample is contacted with said chemiluminescent compound; and
  (iv) a chemiluminescence detector which detects luminescence intensity resulting from contacting said liquid phase atmospheric sample and said chemiluminescent compound and forming a liquid phase atmospheric sample-chemiluminescent compound mixture, wherein said chemiluminescence detector is connected to said contact zone by a contact zone conduit.

2. The apparatus according to claim 1 further comprising a source of said carrier stream for carrying the liquid phase atmospheric sample.

3. The apparatus according to claim 2 wherein the carrier stream is alkaline.

4. The apparatus according to claim 3 wherein the carrier stream further comprises a formate salt.

5. The apparatus according to claim 4 wherein the carrier stream has a minimum pH of about 9 and a maximum pH of about 11.

6. The apparatus according to claim 3 wherein the carrier stream further comprises borax.

7. The apparatus according to claim 6 wherein the carrier stream has a pH of about 9.

8. The apparatus according to claim 1 wherein said carrier stream conduit comprises a fluid director wherein said fluid director is coupled to a fluid pump.

9. The apparatus according to claim 8 wherein said reagent stream conduit comprises a fluid director wherein said fluid director is coupled to a fluid pump.

10. The apparatus according to claim 9 wherein the fluid pump directs the carrier stream and reagent stream at specified flow rates.

11. The apparatus according to claim 10 wherein the flow rates are adjustable.

12. The apparatus according to claim 11 wherein the specified flow rates are independently about 0.5 to 3.0 milliliters per minute.

13. The apparatus according to claim 12 wherein the specified flow rates are independently about 1.0 to 1.5 milliliters per minute.

14. The apparatus according to claim 13 wherein the fluid pump is a peristaltic pump.

15. The apparatus according to claim 1 wherein the scrubbing station comprises said chamber containing housing connected to an air pump having an air outlet, and said housing further containing means for delivery of the liquid phase scrubbant.

16. The apparatus according to claim 15 further comprising a scrubbing element.

17. The apparatus according to claim 16 wherein the scrubbing element comprises a coil.

18. The apparatus according to claim 17 wherein the coil is made of glass.

19. The apparatus according to claim 18 wherein the coil contains five to twenty rounds of coilings.

20. The apparatus according to claim 19 wherein the coil has means for adjusting the coil temperature.

21. The apparatus according to claim 20 wherein the means for adjusting coil temperature is by the flow of a cooling or heating liquid or gas housed within the coil.

22. The apparatus according to claim 15 wherein the liquid phase scrubbant comprises the carrier stream.

23. The apparatus according to claim 1 wherein said contact zone further comprises a mixing station wherein the carrier stream and reagent stream are mixed to form said liquid phase atmospheric sample-chemiluminescent compound mixture.

24. The apparatus according to claim 1 wherein said contact zone further comprises a mixing station within the chemiluminescence detector.

25. The apparatus according to claim 1 further comprising electronics for processing the luminescence intensity.

26. The apparatus according to claim 25 wherein the electronics is a computer or computer system.

27. An apparatus for the quantitative determination of atmospheric hydroperoxyl radical comprising:
(i) a source of a liquid phase atmospheric sample which includes a carrier stream conduit for directing said liquid phase atmospheric sample within a carrier stream wherein said liquid phase atmospheric sample is produced by treating an atmospheric sample with a liquid phase scrubbant in a scrubbing station which comprises a chamber containing housing for said liquid phase scrubbant, wherein said liquid phase scrubbant is capable of dissolving atmospheric hydroperoxyl radical, and wherein said chamber containing housing has an inlet for atmosphere, has an air outlet, and is connected to the carrier stream conduit;
(ii) a source of a chemiluminescent compound in a reagent stream which includes a reagent stream conduit for directing said reagent stream wherein the reagent stream comprises an aqueous-based solvent capable of dissolving the chemiluminescent compound wherein the solvent is a 1:100 volume by volume ethanol to water mixture;
(iii) each of said carrier stream conduit and said reagent stream conduit which are directed to a contact zone whereby said liquid phase atmospheric sample is contacted with said chemiluminescent compound; and
(iv) a chemiluminescence detector which detects luminescence intensity resulting from contacting said liquid phase atmospheric sample and said chemiluminescent compound and forming a liquid phase atmospheric sample-chemiluminescent compound mixture, wherein said chemiluminescence detector is connected to said contact zone by a contact zone conduit.

28. The apparatus according to claim 27 wherein the reagent stream has a pH of about 1 to 3.

29. The apparatus according to claim 28 wherein the reagent stream has a pH of about 2.3.

30. An apparatus for the quantitative determination of atmospheric hydroperoxyl radical comprising:
(i) a source of a liquid phase atmospheric sample which includes a carrier stream conduit for directing said liquid phase atmospheric sample within a carrier stream wherein said liquid phase atmospheric sample is produced by treating an atmospheric sample with a liquid phase scrubbant in a scrubbing station which comprises a chamber containing housing for said liquid phase scrubbant, wherein said liquid phase scrubbant is capable of dissolving atmospheric hydroperoxyl radical, and wherein said chamber containing housing has an inlet for atmosphere, an air outlet, and is connected to the carrier stream conduit;
(ii) a source of a chemiluminescent compound in a reagent stream which includes a reagent stream conduit for directing said reagent stream, wherein the reagent stream comprises an aqueous-based solvent capable of dissolving the chemiluminscent compound;
(iii) each of said carrier stream conduit and said reagent stream conduit which are directed to a contact zone whereby said liquid phase atmospheric sample is contacted with said chemiluminescent compound; and
(iv) a chemiluminescence detector which detects luminescence intensity resulting from contacting said liquid phase atmospheric sample and said chemiluminescent compound, wherein said chemiluminescence detector is connected to said contact zone by a contact zone conduit, and
wherein said chemiluminescence detector further comprises a mixing station wherein the carrier stream and reagent stream are mixed to form a liquid phase atmospheric sample-chemiluminescent compound mixture with a pH of about 3.

31. The apparatus according to claim 30 wherein the chemiluminescent compound luminesces in a reasonably selective manner in the presence of hydroperoxyl radical.

32. The apparatus according to claim 31 wherein the chemiluminescent compound is 2-methyl-6-phenyl-3,7-dihydroimidazo[1,2-α]pyrazin-3-one or 2-methyl-6-(p-methoxyphenyl)-3,7-dihydroimidazo[1,2-α]pyrazin-3-one.

33. The apparatus according to claim 29 wherein the chemiluminescent compound luminesces in a reasonably selective manner in the presence of hydroperoxyl radical.

34. The apparatus according to claim 33 wherein the chemiluminescent compound is 2-methyl-6-phenyl-3,7-dihydroimidazo[1,2-α]pyrazin-3-one or 2-methyl-6-(p-methoxyphenyl)-3,7-dihydroimidazo[1,2-α]pyrazin-3-one.

35. The method according to claim 34 wherein the chemiluminescent compound is in a minimum concentration of about 1 micromolar and a maximum concentration of about 30 micromolar in the chemiluminescent reagent.

36. The apparatus according to claim 35 wherein the chemiluminescent compound is in an amount of about 9 micromolar.

* * * * *